United States Patent [19]

Jessel, Jr. et al.

[11] Plant 4,785

[45] Nov. 3, 1981

[54] GERANIUM PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 175,426

[22] Filed: Aug. 5, 1980

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Koch

[57] ABSTRACT

A new and distinct geranium plant known by the cultivar name Fame and characterized by its scarlet red flower color, medium plant height, short internode length, semi-double flower form, semi-spreading branching pattern, early spring-pot flowering response, prolific outdoor summer flowering traits, good foliage durability, and good flower durability under outdoor summer conditions.

1 Drawing Figure

The present invention comprises a new and distinct cultivar of geranium, a hybrid of the genus Pelargonium, L'Her., hereinafter referred to by the cultivar name Fame.

Fame is a product of a planned breeding program which had the objective of creating new geranium cultivars with red or orange-red flower color, early spring pot flowering period, short plant height, semi-spreading branching pattern, and durable flowers and foliage characteristics under outdoor summer flowering conditions.

Fame was originated from a hybridization made in a controlled breeding program in Barberton, Ohio in 1974. The female parent was an orange-red semi-double seedling (unnamed, #69175001) originated by the present inventors from a hybridization of two unnamed seedlings. The male parent of Fame was a red semi-double seedling (unnamed, #72203003) originated by the present inventors from a hybridization of two unnamed seedlings.

Fame was discovered and selected as one flowering plant within the progeny of the stated cross by Walter H. Jessel, Jr. and William E. Duffett on June 19, 1975 in a controlled environment in Barberton, Ohio.

The first act of asexual reproduction of Fame was accomplished when vegetative cuttings were taken from the initial selection in June, 1975 in a controlled environment by a technician working under formulations established and supervised by Walter H. Jessel, Jr. and William E. Duffett. Horticultural examination of selected units has demonstrated that the combination of characteristics as herein disclosed for Fame are firmly fixed and are retained through successive generations of asexual reproduction.

Fame has not been observed under all possible environmental conditions. The phenotype may vary significantly with variations in environment such as temperature, light intensity, and day length. The following observations, measurements, and comparisons describe plants grown in Barberton, Ohio and in Salinas, Calif. under environmental conditions which approximate those generally used in commercial practice.

The following traits have been repeatedly observed and are determined to be basic characteristics of Fame which in combination distinguish this geranium as a new and distinct cultivar:

1. Scarlet red flower,
2. Medium plant height,
3. Short internode length,
4. Semi-double flower form,
5. Semi-spreading branching pattern,
6. Early spring-pot flowering response (in California),
7. Prolific outdoor summer flowering traits,
8. Good foliage durability under outdoor summer conditions,
9. Good flower durability under outdoor summer conditions, and
10. Dark green foliage color with pronounced dark zonation.

Of the several commercially available geraniums known to the present inventors, the most similar in comparison to Fame are Dark Red Irene (unpatented) and Yours Truly (unpatented). Reference is made to Chart A which compares certain characteristics of Fame with those same characteristics of Dark Red Irene and Yours Truly. General comparisons are as follows:

1. In comparision to Dark Red Irene, Fame has more orange, less blue flower color, smaller average corolla diameter, shorter spring flowering response period (in California), more spreading branching pattern, shorter internode length, and shorter plant height.

2. In comparison to Yours Truly, Fame has less orange flower color, smaller average corolla diameter, shorter spring flowering response period (in California), and shorter internode length. The plant height of Fame is similar to the plant height of Yours Truly.

The accompanying photographic drawing shows typical flower and foliage characteristics of Fame, with colors being as true as possible with illustrations of this type.

In the following description, color references are made to A Limit Color Cascade, by the Munsell Company, 1972 edition. Color values were determined between 11:30 A.M. and 12:00 Noon on March 31, 1980 under 125 foot-candle light intensity at Salinas, Calif.

Botantical classification: A hybrid of the genus Pelargonium, L'Her. cv Fame

I. INFLORESCENCE

A. Umbel:
*Average diameter.*—10 to 13 cm.
*Average depth.*—6 to 7 cm.
*Peduncle length.*—From 16 to 19 cm., averaging 17 cm.
*Pedicel length.*—From 3 to 4 cm.

B. Corolla:
*Average diameter.*—45 mm.
*Form.*—Semi-double; rotate.
*Color (general tonality from a distance of three meters).*—36-13.
*Color (abaxial).*—37-12 to 35-12.
*Color (adaxial).*—37-9 to 37-8, oxidizing with maturity to 36-10 over 36-8.

C. Bud:
*Shape.*—Conodial.
*Color (abaxial).*—35-12.
*Color (adaxial).*—35-12.

D. Reproductive organs:
*Androecium.*—Monodelphous, dorsifixed, pentadynamous stamen, scant to moderate pollen.
*Gynoecium.*—5-lobed, linear stigma; pubescent, 5-loculed carpel.

E. Spring flowering response period:
*Ohio.*—Late, 50% of plants with at least 1 flower open 9 weeks after stick of unrooted cutting.
*California.*—Early, 90% of plants with at least 1 flower open 8 weeks after stick of unrooted cutting.

F. Outdoor flower production: Good; flower count in 1974 averaged between 1.8 and 3.2 flowers per plant for June through September observation period.

G. Durability:
*Shatter resistance.*—Good.
*Tolerance of botrytis.*—Good.

II. PLANT

A. Foliage:
*Form.*—Reni-form.
*Margin.*—Undulate; crenate.
*Color (abaxial).*—21-14 to 21-15.

*Color (adaxial).*—21-14 overlaid with white.
*Color (zonation).*—21-14 to 21-15.
*Tolerance of botrytis.*—Good.

B. General appearance and form:
*Internode length.*—Short.
*Branching pattern.*—Semi-spreading, produces mound type growth.
*Height.*—Medium.

CHART A.

COMPARISON OF FAME, DARK RED IRENE AND YOURS TRULY

| CULTIVAR | COROLLA COLOR | AVERAGE COROLLA DIAMETER | CALIFORNIA SPRING FLOWERING RESPONSE |
|---|---|---|---|
| FAME | Scarlet Red | 45 mm. | Early |
| DARK RED IRENE | Dark Red Oxidizing with blush overtones | 72 mm. | Late |
| YOURS TRULY | Orange Red | 50 mm. | Mid-Season |

| CULTIVAR | BRANCHING HABIT | INTERNODE LENGTH | PLANT HEIGHT |
|---|---|---|---|
| FAME | Semi-Spreading | Short | Medium |
| DARK RED IRENE | Upright | Long | Tall |
| YOURS TRULY | Semi-Spreading | Medium | Medium |

COMPARISONS MADE BETWEEN NON-PINCHED PLANTS GROWN IN SALINAS, CALIFORNIA AND IN BARBERTON, OHIO.

We claim:

1. A new and distinct geranium plant, a hybrid of the genus Pelargonium, L'Her., referred to by the cultivar name Fame, as described and illustrated, and characterized by the combination of characteristics of scarlet red flower color; medium plant height; short internode length; semi-double flower form; semi-spreading branching pattern; early spring-pot flowering response; prolific outdoor summer flowering traits; good foliage durability; good flower durability; and dark green foliage color with pronounced dark zonation.

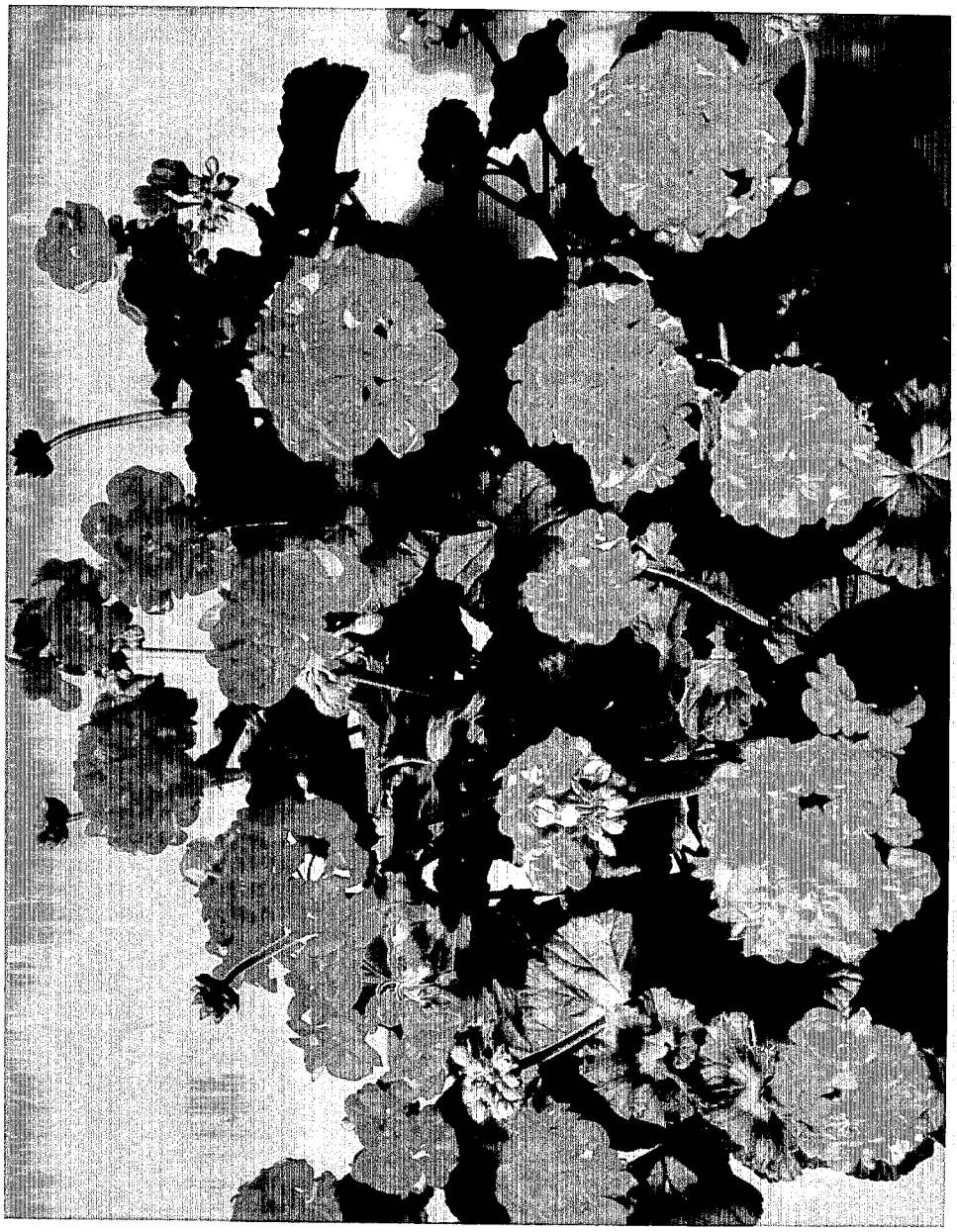

* * * * *